(12) United States Patent
Robertson et al.

(10) Patent No.: US 11,641,958 B2
(45) Date of Patent: May 9, 2023

(54) BLANKET WITH VARIABLY WEIGHTED ZONES

(71) Applicant: CVB INC, Logan, UT (US)

(72) Inventors: Kyle Lamar Robertson, Providence, UT (US); Tony Johnson Roberts, Providence, UT (US); Jacob David Ozmun, Nibley, UT (US)

(*) Notice: Subject to any disclaimer, the term of this patent is extended or adjusted under 35 U.S.C. 154(b) by 273 days.

(21) Appl. No.: 16/881,280

(22) Filed: May 22, 2020

(65) Prior Publication Data

US 2021/0361092 A1 Nov. 25, 2021

(51) Int. Cl.
| | |
|---|---|
| A47G 9/02 | (2006.01) |
| A61M 21/02 | (2006.01) |
| A61M 21/00 | (2006.01) |

(52) U.S. Cl.
CPC ......... *A47G 9/0223* (2013.01); *A47G 9/0207* (2013.01); *A61M 21/02* (2013.01); *A61M 2021/0022* (2013.01)

(58) Field of Classification Search
CPC .......... A47G 9/00; A47G 9/02; A47G 9/0207; A47G 9/0223; A61M 2021/0022; A61M 21/02
See application file for complete search history.

(56) References Cited

U.S. PATENT DOCUMENTS

| | | | | |
|---|---|---|---|---|
| 4,839,934 A * | 6/1989 | Rojas | ................... | A47G 9/0207 5/486 |
| 2007/0226905 A1* | 10/2007 | VanNeste | ............... | A47G 9/023 5/486 |
| 2007/0277315 A1* | 12/2007 | Loh | ....... | A47G 9/0207 5/486 |
| 2010/0024125 A1* | 2/2010 | Li | ............... | A47G 9/02 5/413 R |
| 2011/0047698 A1* | 3/2011 | Parker | .................. | A47G 9/0207 112/475.08 |
| 2015/0013068 A1* | 1/2015 | Werthaiser | ........... | A47G 9/0207 5/502 |
| 2015/0366734 A1* | 12/2015 | Kjell | ...................... | A61M 21/02 601/84 |
| 2018/0035832 A1* | 2/2018 | Ureten | .................. | A61M 21/02 |
| 2019/0021525 A1* | 1/2019 | Hamm | ................. | A47G 9/0223 |
| 2020/0170424 A1* | 6/2020 | Xu | ........................ | A47G 9/0223 |
| 2020/0236907 A1* | 7/2020 | Nilsson | ................ | A47G 9/0223 |

OTHER PUBLICATIONS

International Search Report and Written Opinion of the International Searching Authority for International Patent App. No. PCT/US2021/033103 dated Aug. 18, 2021 (7 pages).

* cited by examiner

*Primary Examiner* — David R Hare
*Assistant Examiner* — George Sun

(57) ABSTRACT

A weighted blanket that includes a multilayered fabric of a predetermined width and a predetermined length; a plurality of distinct zones formed in the fabric, wherein the zones are adjacent to one another; and weighted material placed between the fabric layers within each zone, wherein the relative weight of the zones is non-uniform. The blanket may further comprise a plurality of compartments formed across each zone, wherein the compartments are operative to minimize movement of the weighted material. The blanket may further comprise padding placed around the weighted material within the zones.

6 Claims, 5 Drawing Sheets

BLANKET WITH VARIABLY WEIGHTED ZONES

BACKGROUND

The disclosed inventive subject matter relates in general to devices and items used as blankets and more specifically to a blanket or similar item having variably weighted zones with the structure of the blanket or similar item.

Weighted blankets, comforters, and covers have recently become popular commercial products due to stress-relieving or anxiety-reducing effects often experienced by the users of such products. In addition to foam, fiber, or similar materials typically used as stuffing, weighted blankets are often filled in a uniform manner with plastics or other materials that provide additional weight to such blankets. When used, these weighted or "gravity" blankets are perceived by some as replicating the calming effects of a "hug" received from another person. While these products have proven to be commercially successful, the uniformly distributed weight of the plastic or other material placed within the blanket may actually be uncomfortable or otherwise undesirable to some consumers. For example, while a significant amount of additional weight placed over a person's midsection may be pleasing, the same amount of weight placed over a person's face, neck, or legs may be constricting or otherwise unpleasant. Accordingly, non-uniformly weighted or variably weighted blankets, comforters, and covers would be desirable as commercial and/or therapeutic products.

SUMMARY

The following provides a summary of certain example implementations of the disclosed inventive subject matter. This summary is not an extensive overview and is not intended to identify key or critical aspects or elements of the disclosed inventive subject matter or to delineate its scope. However, it is to be understood that the use of indefinite articles in the language used to describe and claim the disclosed inventive subject matter is not intended in any way to limit the described inventive subject matter. Rather the use of "a" or "an" should be interpreted to mean "at least one" or "one or more".

One implementation provides a blanket. This blanket comprises a multilayered fabric of a predetermined width and a predetermined length; a plurality of distinct zones formed in the fabric, wherein the zones are adjacent to one another; and weighted material placed between the fabric layers within each zone, wherein the relative weight of the zones is non-uniform. The blanket may further comprise a plurality of compartments formed across each zone, wherein the compartments are operative to minimize movement of the weighted material. The blanket may further comprise padding or other material placed around the weighted material within the zones. The weighted material may include glass beads of predetermined sizes and predetermined weights or metal beads of predetermined sizes and predetermined weights. The number of zones may be in the range of two zones to ten zones or more. The fabric may include natural fibers, synthetic fibers, or a combination of natural and synthetic fibers.

Another implementation provides a weighted blanket. This weighted blanket comprises an upper fabric layer having a predetermined width and predetermined length; a lower fabric layer having a predetermined width and a predetermined length; a plurality of adjacent zones formed along the length of the upper and lower fabric layers, wherein the zones are separated from one another by stitching formed in the upper and lower fabric layers; and a predetermined amount of weighted material placed within each zone, wherein the weight of a zone differs from the weight of an adjacent zone or other zones within the blanket. The weighted blanket may also comprise a first layer of padding disposed between the upper layer of fabric and the weighted material; and a second layer of padding disposed between the lower layer of fabric and the weighted material. Each zone may be subdivided widthwise into separate compartments by stitching formed in the upper and lower layers of fabric, wherein the compartments are operative to minimize movement of the weighted material. The weighted material may include glass beads of predetermined sizes and predetermined weights or metal beads of predetermined sizes and predetermined weights. The number of zones may be in the range of two zones to ten zones or more. The fabric may include natural fibers, synthetic fibers, or a combination of natural and synthetic fibers.

Still another implementation provides another weighted blanket. This weighted blanket comprises an upper layer of fabric having a predetermined width and a predetermined length; a first layer of padding having a predetermined width and a predetermined length positioned beneath the upper layer of fabric; a lower layer of fabric having a predetermined width and a predetermined length; a second layer of padding having a predetermined width and a predetermined length positioned above the lower layer of fabric; a plurality of adjacent zones formed along the length of the upper and lower layers of fabric and along the length of the first and second layers of padding, wherein the zones are separated from one another by stitching formed in the upper and lower layers of fabric and first and second layers of padding; and a predetermined amount of weighted material placed within each zone, wherein the weight of a zone differs from the weight of an adjacent zone or other zones within the blanket. Each zone may be subdivided widthwise into separate compartments by stitching formed in the upper and lower layers, wherein the compartments are operative to minimize movement of the weighted material. The weighted material may include glass beads of predetermined sizes and predetermined weights or metal beads of predetermined sizes and predetermined weights. The number of zones may be in the range of two zones to ten zones or more. The fabric may include natural fibers, synthetic fibers, or a combination of natural and synthetic fibers.

It should be appreciated that all combinations of the foregoing concepts and additional concepts discussed in greater detail below (provided such concepts are not mutually inconsistent) are contemplated as being part of the inventive subject matter disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more example implementations of the disclosed inventive subject matter and, together with the general description given above and detailed description given below, serve to explain the principles of the disclosed subject matter, and wherein.

DETAILED DESCRIPTION

Figure 1A:
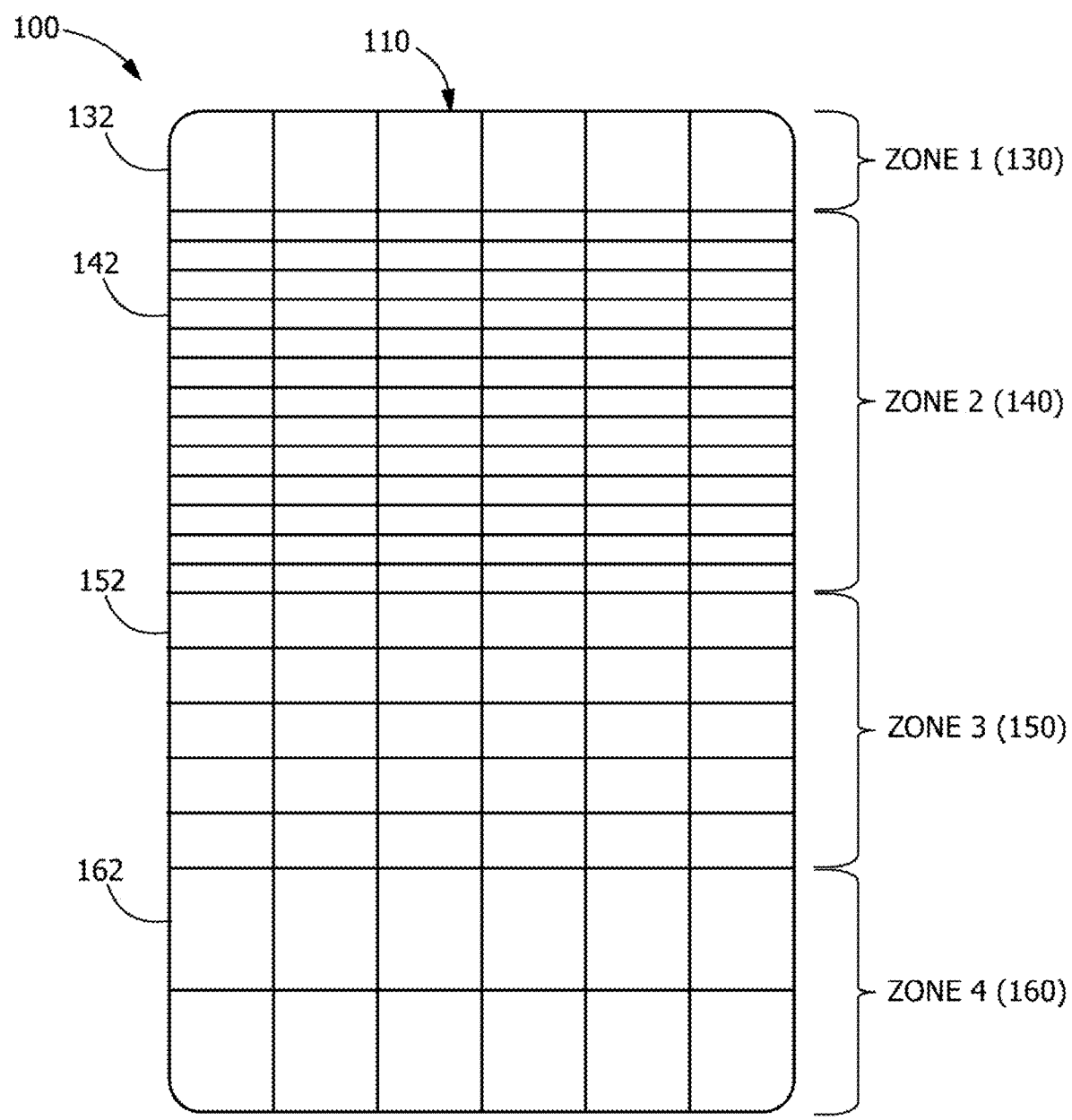
FIG. 1A is a top view of a first example implementation of a weighted blanket.

Example implementations are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the disclosed inventive subject matter. Accordingly, the following implementations are set forth without any loss of generality to, and without imposing limitations upon, the claimed subject matter.

Disclosed herein are various implementations of a blanket, comforter, bedspread, cover, or similar item that includes separate, multiple zones defined lengthwise therein, wherein each zone has a weight that is different than the zone to which it is immediately adjacent. Weighted blankets typically provide uniform weight distribution; however, the weighted items disclosed herein allow blanket weight to be non-uniformly allocated to certain locations within the blanket. For example, more of the blanket's total weight may be allocated to the region of the blanket corresponding to a person's chest or mid-section and less weight may be allocated to the region of the blanket corresponding to a person's knees or feet. Effectiveness or usefulness of the weighted blanket is thereby increased by distributing its weight to be more consistent with the weight distribution of the human body, in certain examples.

Figure 1B:
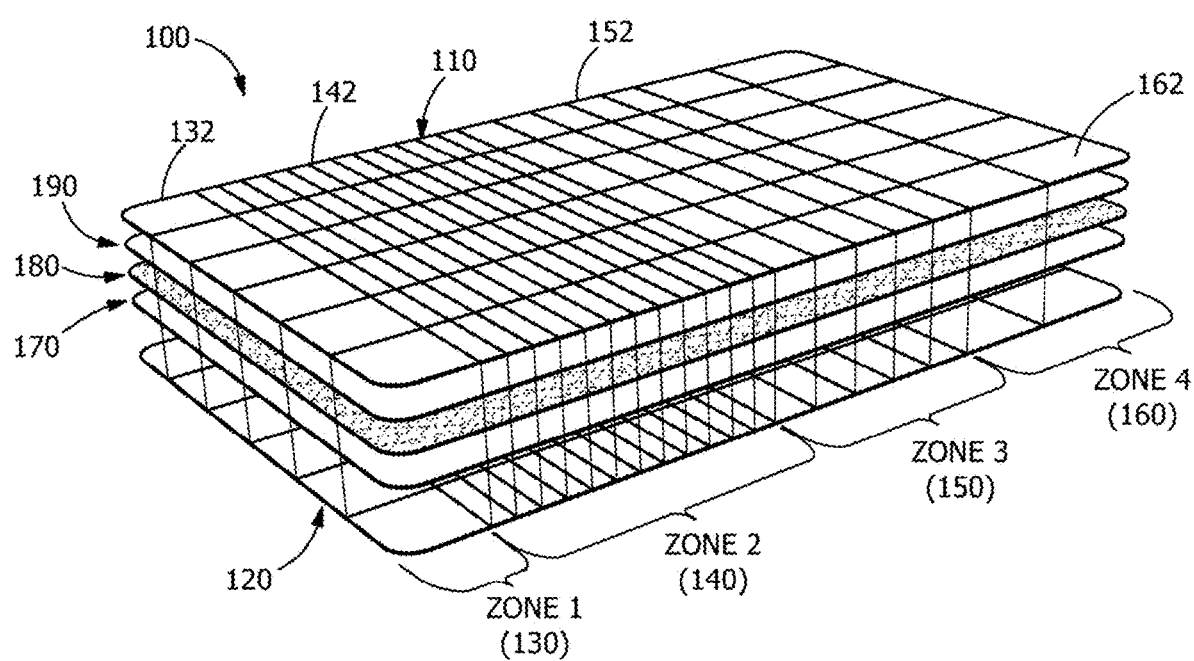
FIG. 1B is an exploded side perspective view of the weighted blanket of FIG. 1A.
Figure 2:
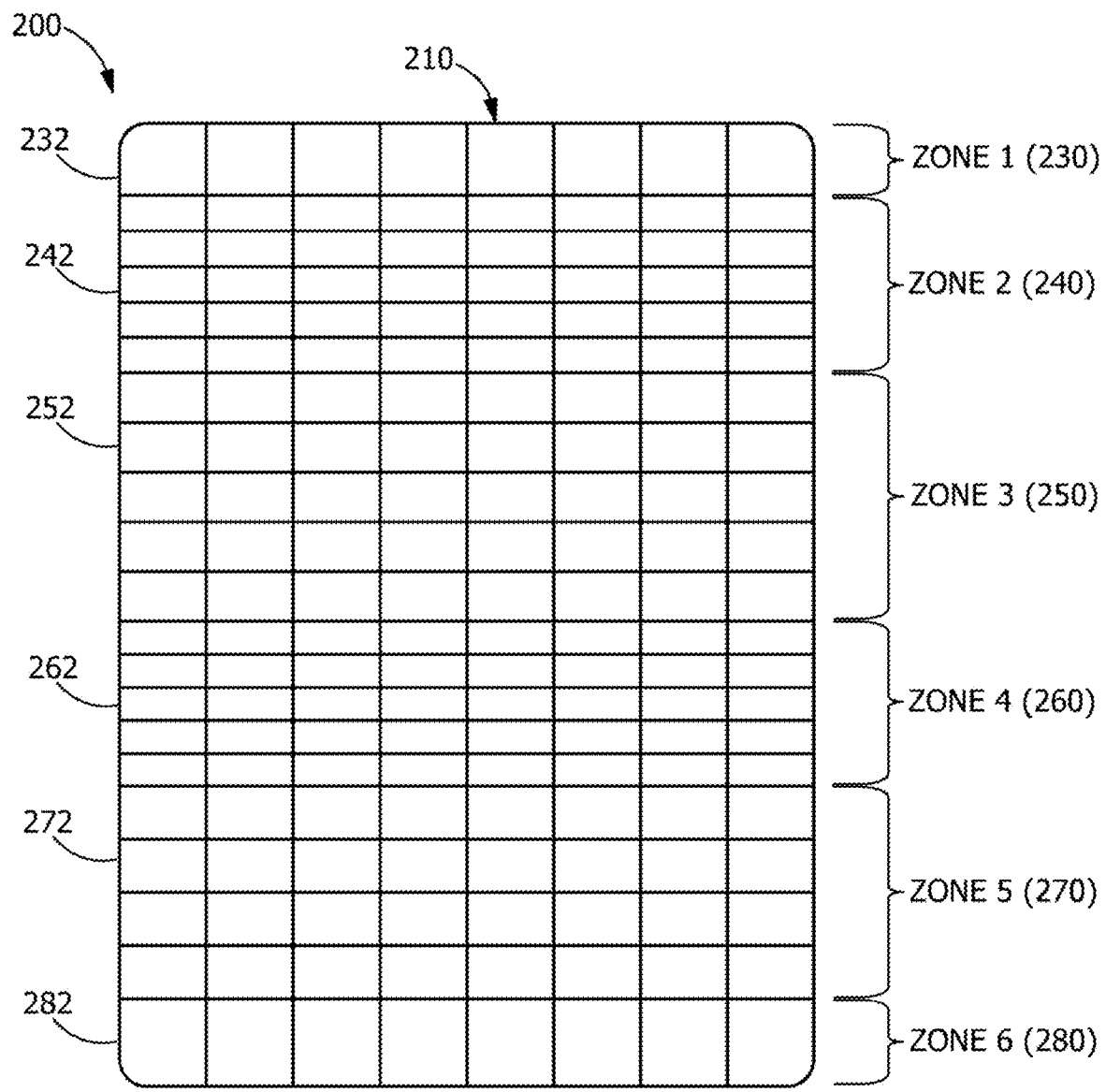
FIG. 2 is a top view of a second example implementation of a weighted blanket.
Figure 3:
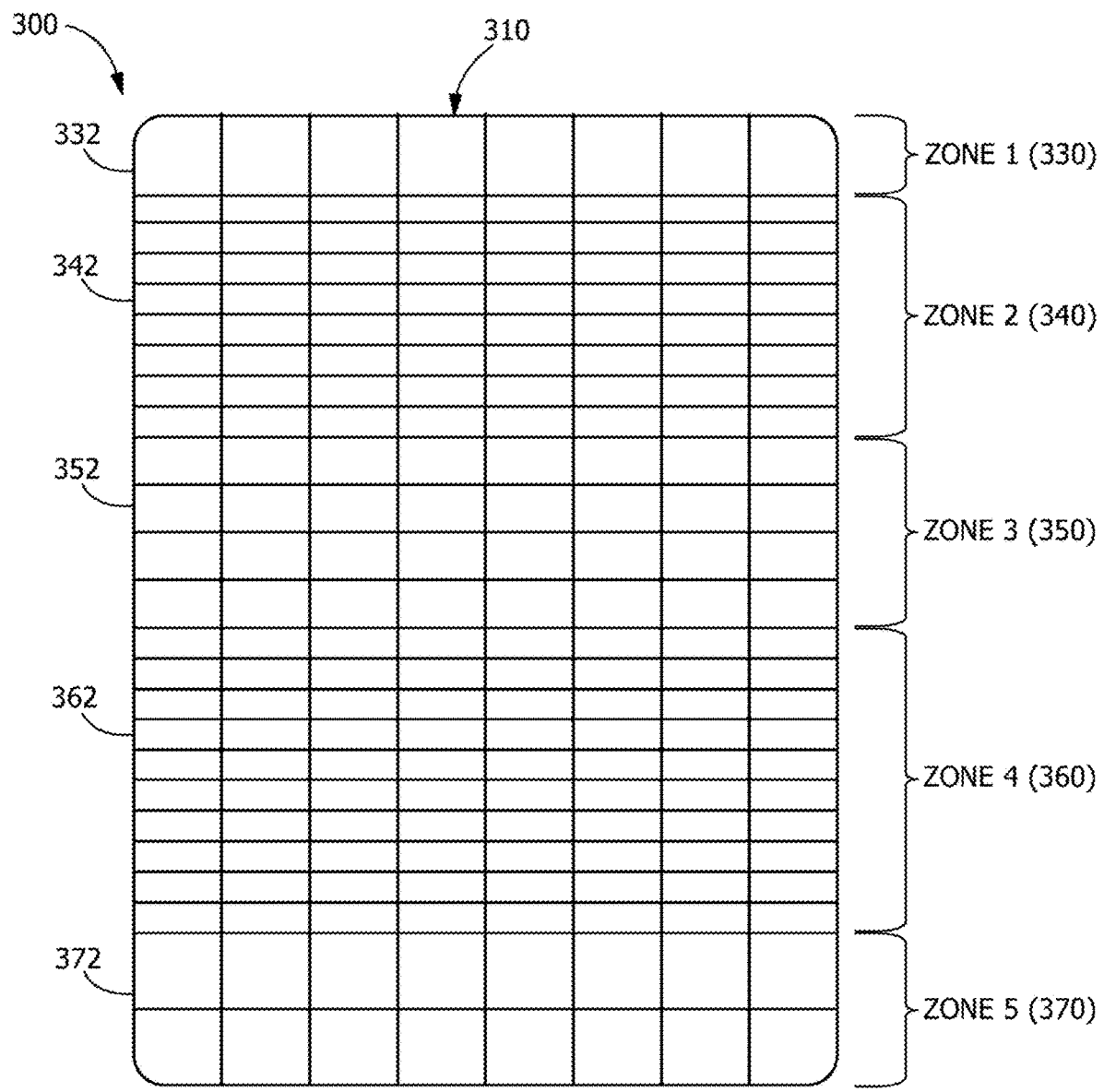
FIG. 3 is a top view of a third example implementation of a weighted blanket.
Figure 4:
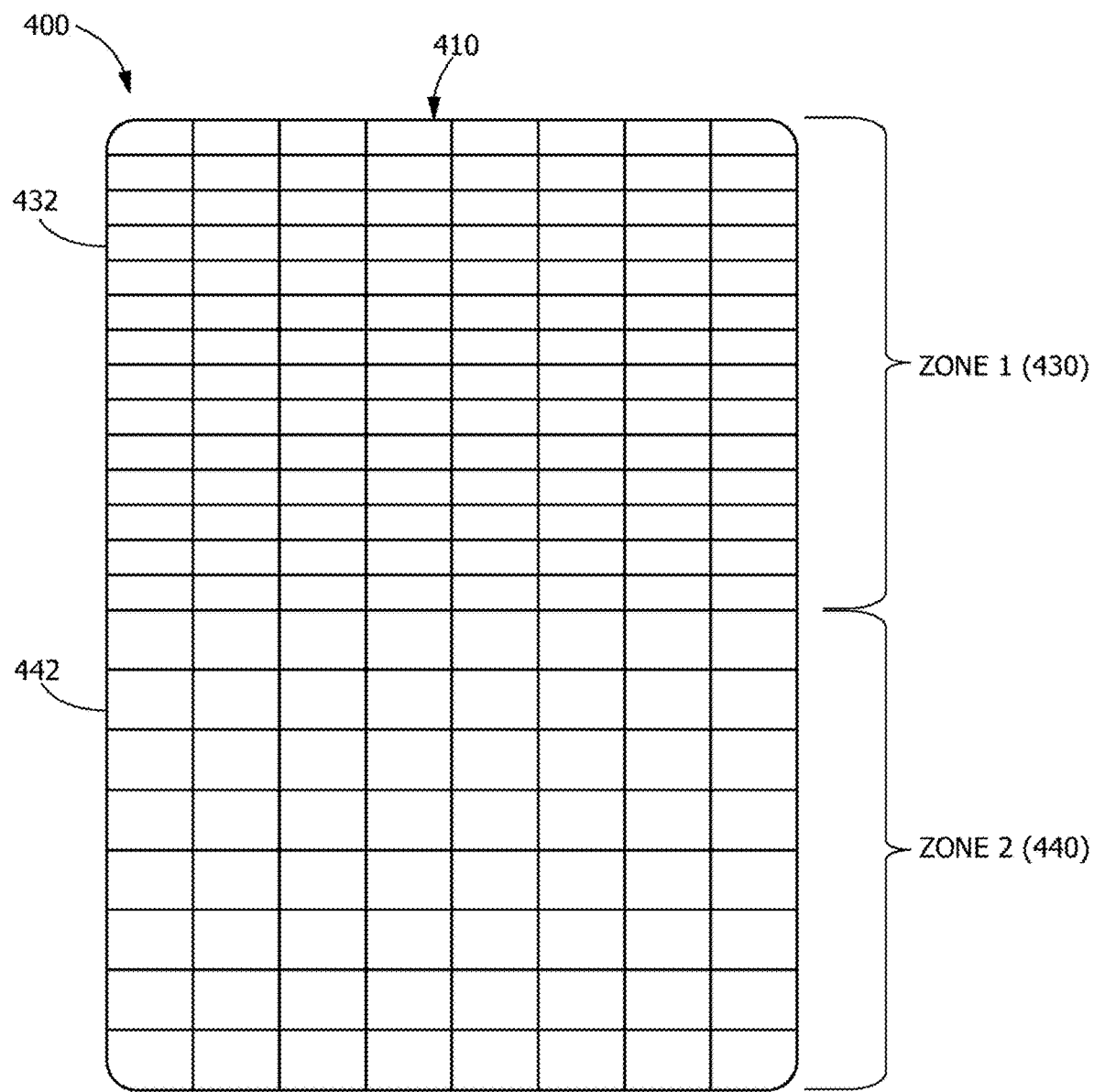
FIG. 4 is a top view of a fourth example implementation of a weighted blanket.

With reference to the Figures, various implementations of a blanket with variably weighted (i.e., non-uniform) zones formed therein are shown. FIG. 1A provides a top view of a first example implementation of a weighted blanket; and FIG. 1B provides an exploded side perspective view of the weighted blanket of FIG. 1A. In this implementation, the bottom side or portion of the blanket shown in the Figure has the same stitching or quilting pattern as the top side or portion of the blanket. FIG. 2 provides a top view of a second example implementation of a weighted blanket; FIG. 3 provides a top view of a third example implementation of a weighted blanket; and FIG. 4 provides a top view of a fourth example implementation of a weighted blanket. In the implementations shown in FIGS. 2-4, the bottom side or portion of the blanket shown in each Figure has the same stitching or quilting pattern as the top side or portion of the blanket.

As previously stated, FIG. 1A provides a top view of a first example implementation of a weighted blanket; and FIG. 1B provides an exploded side perspective view of the weighted blanket of FIG. 1A. In these Figures, weighted blanket 100 includes top portion 110, which is typically formed from a fabric having natural fibers, synthetic fibers, or a combination of natural and synthetic fibers; and bottom portion 120, which also is typically formed from a fabric having natural fibers, synthetic fibers, or a combination of natural and synthetic fibers. Weighted blanket 100 includes a plurality of separate or distinct zones defined along the length of the blanket and each of these zones is weighted in a predetermined manner. The weight of a particular zone is typically different than the weight of an adjacent zone although in certain implementations, the weight of adjacent zone could be the same. The implementation shown in FIGS. 1A-1B includes four differently weighted zones. First weighted zone 130 includes no additional weight beyond the weight of the blanket itself. First weighted zone 130 is subdivided into a plurality of compartments 132 using stitching or quilting techniques. Second weighted zone 140 includes weighted material that adds an additional eight (8) pounds to this zone of weighted blanket 100. Second weighted zone 140 is subdivided into a plurality of compartments 142 using stitching or quilting techniques. Compartments 142 are operative to stabilize or immobilize the weighted material in second weighted zone 140 so that this material does not redistribute itself elsewhere within weighted blanket 100. Third weighted zone 150 includes weighted material that adds an additional five (5) pounds to this zone of weighted blanket 100. Third weighted zone 150 is subdivided into a plurality of compartments 152 using stitching or quilting techniques. Compartments 152 are operative to stabilize or immobilize the weighted material in third weighted zone 150 so that this material does not redistribute itself elsewhere within weighted blanket 100. Fourth weighted zone 160 includes weighted material that adds an additional two (2) pounds to this zone of weighted blanket 100. Fourth weighted zone 160 is subdivided into a plurality of compartments 162 using stitching or quilting techniques. Compartments 162 are operative to stabilize or immobilize the weighted material in third weighted zone 160 so that this material does not redistribute itself elsewhere within weighted blanket 100. Weighted blanket 100 may be manufactured in any desired size and may be square, rectangular, or any other desired shape.

With reference to FIG. 1B, an example method for making weighted blanket 100 includes defining the desired weight zones on bottom portion 120 and placing lower padding layer 170 on bottom portion 120. Weighted material 180, which may be glass or metal beads of various sizes or diameters (or any other suitable material), is weighed out and then evenly distributed on top of lower padding layer 170 in each predefined zone where additional weight is desired. Upper padding layer 190 is then placed on top of the weighed material that has been distributed on lower padding layer 170 and top portion 110 is placed on top of upper padding layer 190. A quilting machine or similar device is then used to create the desired quilting pattern and the edges of the blanket are closed to create the final product. The "padding" of lower padding layer 170 and upper padding layer 190 may include batting, wadding, or stuffing made from polyester, cotton, or any other suitable material or combinations of materials that add thickness, texture, or softness to the blanket. The other implementations disclosed herein (i.e., those shown in FIGS. 2-4) may be manufactured using the disclosed method.

FIG. 2 provides a top view of a second example implementation of a weighted blanket. Weighted blanket 200 includes top portion 210, which is typically formed from a fabric having natural fibers, synthetic fibers, or a combination of natural and synthetic fibers; and bottom portion 220 (not shown), which also is typically formed from a fabric having natural fibers, synthetic fibers, or a combination of natural and synthetic fibers. Weighted blanket 200 includes a plurality of separate or distinct zones defined along the length of the blanket and each of these zones is weighted in a predetermined manner. The weight of a particular zone is typically different than the weight of an adjacent zone. The implementation shown in FIG. 2 includes six differently weighted zones. First weighted zone 230 includes weighted material that adds an additional two (2) pounds to this zone of weighted blanket 200. First weighted zone 230 is subdivided into a plurality of compartments 232 using stitching or quilting techniques. Second weighted zone 240 includes weighted material that adds an additional six (6) pounds to this zone of weighted blanket 200. Second weighted zone 240 is subdivided into a plurality of compartments 242 using stitching or quilting techniques. Compartments 242 are operative to stabilize or immobilize the weighted material in second weighted zone 240 so that this material does not redistribute itself elsewhere within weighted blanket 200. Third weighted zone 250 includes weighted material that adds an additional three (3) pounds to this zone of weighted blanket 200. Third weighted zone 250 is subdivided into a plurality of compartments 252 using stitching or quilting techniques. Compartments 252 are operative to stabilize or immobilize the weighted material in third weighted zone 250 so that this material does not redistribute itself elsewhere within weighted blanket 200. Fourth weighted zone 260 includes weighted material that adds an additional six (6) pounds to this zone of weighted blanket 200. Fourth weighted zone 260 is subdivided into a plurality of compartments 262 using stitching or quilting techniques. Compartments 262 are operative to stabilize or immobilize the weighted material in third weighted zone 260 so that this material does not redistribute itself elsewhere within weighted blanket 200. Fifth weighted zone 270 includes weighted material that adds an additional three (3) pounds to this zone of weighted blanket 200. Fifth weighted zone 270 is subdivided into a plurality of compartments 272 using stitching or quilting techniques. Compartments 272 are operative to stabilize or immobilize the weighted material in third weighted zone 270 so that this material does not redistribute itself elsewhere within weighted blanket 200. Sixth weighted zone 280 includes no additional weight beyond the weight of the blanket itself. Sixth weighted zone 280 is subdivided into a plurality of compartments 282 using stitching or quilting techniques. Weighted blanket 200 may be manufactured in any desired size and may be square, rectangular, or any other desired shape. In one implementation, weighted blanket 200 is 72 inches in length and 48 inches in width.

FIG. 3 provides a top view of a third example implementation of a weighted blanket. Weighted blanket 300 includes top portion 310, which is typically formed from a fabric having natural fibers, synthetic fibers, or a combination of natural and synthetic fibers; and bottom portion 330 (not shown), which also is typically formed from a fabric having natural fibers, synthetic fibers, or a combination of natural and synthetic fibers. Weighted blanket 300 includes a plurality of separate or distinct zones defined along the length of the blanket and each of these zones is weighted in a predetermined manner. The weight of a particular zone is typically different than the weight of an adjacent zone. The implementation shown in FIG. 3 includes five differently weighted zones. First weighted zone 330 includes weighted material that adds an additional one (1) pound to this zone of weighted blanket 300. First weighted zone 330 is subdivided into a plurality of compartments 332 using stitching or quilting techniques. Compartments 332 are operative to stabilize or immobilize the weighted material in first weighted zone 330 so that this material does not redistribute itself elsewhere within weighted blanket 300. Second weighted zone 340 includes weighted material that adds an additional seven (7) pounds to this zone of weighted blanket 300. Second weighted zone 340 is subdivided into a plurality of compartments 342 using stitching or quilting techniques. Compartments 342 are operative to stabilize or immobilize the weighted material in second weighted zone 340 so that this material does not redistribute itself elsewhere within weighted blanket 300. Third weighted zone 350 includes weighted material that adds an additional three (3) pounds to this zone of weighted blanket 300. Third weighted zone 350 is subdivided into a plurality of compartments 352 using stitching or quilting techniques. Compartments 352 are operative to stabilize or immobilize the weighted material in third weighted zone 350 so that this material does not redistribute itself elsewhere within weighted blanket 300. Fourth weighted zone 360 includes weighted material that adds an additional five (5) pounds to this zone of weighted blanket 300. Fourth weighted zone 360 is subdivided into a plurality of compartments 362 using stitching or quilting techniques. Compartments 362 are operative to stabilize or immobilize the weighted material in third weighted zone 360 so that this material does not redistribute itself elsewhere within weighted blanket 300. Fifth weighted zone 370 includes weighted material that adds an additional two (2) pounds to this zone of weighted blanket 200. Fifth weighted zone 370 is subdivided into a plurality of compartments 372 using stitching or quilting techniques. Compartments 372 are operative to stabilize or immobilize the weighted material in third weighted zone 370 so that this material does not redistribute itself elsewhere within weighted blanket 300. Weighted blanket 300 may be manufactured in any desired size and may be square, rectangular, or any other desired shape. In one implementation, weighted blanket 300 is 72 inches in length and 48 inches in width.

FIG. 4 provides a top view of a fourth example implementation of a weighted blanket. Weighted blanket 400 includes top portion 410, which is typically formed from a fabric having natural fibers, synthetic fibers, or a combination of natural and synthetic fibers; and bottom portion 430 (not shown), which also is typically formed from a fabric having natural fibers, synthetic fibers, or a combination of natural and synthetic fibers. Weighted blanket 400 includes a plurality of separate or distinct zones defined along the length of the blanket and each of these zones is weighted in a predetermined manner. The weight of a particular zone is typically different than the weight of an adjacent zone. The implementation shown in FIG. 4 includes two differently weighted zones. First weighted zone 430 includes weighted material that adds an additional eight (8) pounds to this zone of weighted blanket 400. First weighted zone 430 is subdivided into a plurality of compartments 432 using stitching or quilting techniques. Compartments 432 are operative to stabilize or immobilize the weighted material in first weighted zone 430 so that this material does not redistribute itself elsewhere within weighted blanket 400. Second weighted zone 440 includes weighted material that adds an additional four (4) pounds to this zone of weighted blanket 400. Second weighted zone 440 is subdivided into a plurality of compartments 442 using stitching or quilting techniques. Compartments 442 are operative to stabilize or immobilize the weighted material in second weighted zone 440 so that this material does not redistribute itself elsewhere within weighted blanket 400. Weighted blanket 400 may be manufactured in any desired size and may be square, rectangular, or any other desired shape. In one implementation, weighted blanket 400 is 72 inches in length and 48 inches in width.

In various implementations of the disclosed weighted blanket, the weighted zones may be visually differentiated from one another using different fabric types, different fabric colors, different patterns printed on the fabric, or unique tags placed on each zone. Visually differentiation of zones may also be accomplished by using different stitching or quilting patterns for each zone. The use of tighter quilting patterns for heavier zones within the weighted blanket also facilitates immobilization of the weighted material within the zone. The weighted material may include plastic or glass beads having a sand-like texture. However, other materials may be used to increase the weight of the blanket such as larger plastic beads, metal beads, ceramic beads, buckwheat hulls or other natural fillers, and/or additional heavier fabrics such as, for example, felt. The disclosed weighted blankets are scalable and may be manufactured in many different dimensions and different shapes, if desired. Zone sizes, zone weights, and zone quilting patterns may be used in many different combinations to create customized blankets for particular types of users or for specific applications. Finally, in some implementations, duvet loops are included at the corners and/or along the edges of the blanket.

Any literature and similar material cited in this application, including, but not limited to, patents, patent applications, articles, books, treatises, and web pages, regardless of the format of such literature and similar materials, are expressly incorporated by reference in their entirety. In the event that one or more of the incorporated references and similar materials differs from or contradicts this application, including but not limited to defined terms, term usage, described techniques, or the like, this application controls.

As previously stated and as used herein, the singular forms "a," "an," and "the," refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this specification are used to describe and account for small fluctuations, such as due to variations in processing. For example, these terms can refer to less than or equal to ±5%, such as less than or equal to ±2%, such as less than or equal to ±2%, such as less than or equal to ±0.5%, such as less than or equal to ±0.2%, such as less than or equal to ±0.2%, such as less than or equal to ±0.05%, and/or 0%.

Underlined and/or italicized headings and subheadings are used for convenience only, do not limit the disclosed subject matter, and are not referred to in connection with the interpretation of the description of the disclosed subject matter. All structural and functional equivalents to the elements of the various implementations described throughout this disclosure that are known or later come to be known to those of ordinary skill in the art are expressly incorporated herein by reference and intended to be encompassed by the disclosed subject matter. Moreover, nothing disclosed herein is intended to be dedicated to the public regardless of whether such disclosure is explicitly recited in the above description.

There may be many alternate ways to implement the disclosed inventive subject matter. Various functions and elements described herein may be partitioned differently from those shown without departing from the scope of the disclosed inventive subject matter. Generic principles defined herein may be applied to other implementations. Different numbers of a given module or unit may be employed, a different type or types of a given module or unit may be employed, a given module or unit may be added, or a given module or unit may be omitted.

It should be appreciated that all combinations of the foregoing concepts and additional concepts discussed in greater detail herein (provided such concepts are not mutually inconsistent) are contemplated as being part of the disclosed inventive subject matter. In particular, all combinations of claimed subject matter appearing at the end of this disclosure are contemplated as being part of the inventive subject matter disclosed herein. While the disclosed inventive subject matter has been illustrated by the description of example implementations, and while the example implementations have been described in certain detail, there is no intention to restrict or in any way limit the scope of the appended claims to such detail. Additional advantages and modifications will readily appear to those skilled in the art. Therefore, the disclosed inventive subject matter in its broader aspects is not limited to any of the specific details, representative devices and methods, and/or illustrative examples shown and described. Accordingly, departures may be made from such details without departing from the spirit or scope of the general inventive concept.

What is claimed:
1. A blanket, comprising:
   (a) a multilayered fabric of a predetermined width and a predetermined length;
   (b) a plurality of visually distinct zones formed in the fabric that extend the entire width of the fabric, wherein the zones are adjacent to one another, wherein the zones are perpendicular to the predetermined length of the multilayered fabric, and wherein the size of each zone differs from the size of the other zones;
   (c) weighted material placed between the fabric layers of each zone, wherein the amount of weighted material placed in each zone differs from the amount of weighted material placed in the other zones; and
   (d) a plurality of quilted, material-immobilizing compartments formed within each weighted zone, wherein each plurality of quilted, material-immobilizing compartments stabilizes the weight of an individual weighted zone, wherein the size of the compartments is uniform within each weighted zone, and wherein the size of the compartments from zone to zone is non-uniform.

2. The blanket of claim 1, further comprising padding placed around the weighted material within the zones.

3. The blanket of claim 1, wherein the weighted material includes glass beads of predetermined sizes and predetermined weights.

4. The blanket of claim 1, wherein the weighted material includes metal beads of predetermined sizes and predetermined weights.

5. The blanket of claim 1, wherein the number of zones is in the range of two zones to ten zones.

6. The blanket of claim 1, wherein the fabric includes natural fibers, synthetic fibers, or a combination of natural and synthetic fibers.

\* \* \* \* \*